United States Patent
Lesage et al.

(10) Patent No.: US 9,134,229 B2
(45) Date of Patent: Sep. 15, 2015

(54) METHOD AND SYSTEM FOR OPTICAL DATA ACQUISITION AND TOMOGRAPHY IMAGING OF A TURBID MEDIUM OBJECT

(75) Inventors: Frédéric Lesage, Montréal (CA); Samuel Bélanger, St-Bruno (CA); Maxime Abran, Montréal (CA); Jean Provost, Brossard (CA)

(73) Assignee: POLYVALOR, LIMITED PARTNERSHIP, Montreal, QC (CA)

( * ) Notice: Subject to any disclaimer, the term of this patent is extended or adjusted under 35 U.S.C. 154(b) by 607 days.

(21) Appl. No.: 13/497,290

(22) PCT Filed: Sep. 22, 2010

(86) PCT No.: PCT/CA2010/001445
§ 371 (c)(1),
(2), (4) Date: May 31, 2012

(87) PCT Pub. No.: WO2011/035408
PCT Pub. Date: Mar. 31, 2011

(65) Prior Publication Data
US 2012/0236310 A1  Sep. 20, 2012

Related U.S. Application Data

(60) Provisional application No. 61/244,589, filed on Sep. 22, 2009.

(51) Int. Cl.
*G01N 21/59* (2006.01)
*G01N 21/47* (2006.01)
(Continued)

(52) U.S. Cl.
CPC .......... *G01N 21/4795* (2013.01); *A61B 5/0073* (2013.01); *A61B 5/0091* (2013.01); *A61B 5/4312* (2013.01); *G01N 2021/1787* (2013.01)

(58) Field of Classification Search
USPC .............. 356/432, 436, 39–41; 600/310, 341, 600/473
See application file for complete search history.

(56) References Cited

U.S. PATENT DOCUMENTS 6,657,758 B1 * 12/2003 Garner ........................ 359/196.1
6,665,557 B1 * 12/2003 Alfano et al. ................. 600/473
(Continued)

OTHER PUBLICATIONS

A. Bassi, C. D'Andrea, G. Valentini, R. Cubeddu, and S. Arridge, "Temporal propagation of spatial information in turbid media," Optics Letters, vol. 33, Dec. 2008, pp. 2836-2838.
(Continued)

*Primary Examiner* — Sang Nguyen
(74) *Attorney, Agent, or Firm* — Anglehart et al.

(57) ABSTRACT

A system and method for optical data acquisition of an illuminated turbid medium object, the system comprises a variable structured light detector and a controller. The light detector is adapted to retrieve light from a plurality of detection points of an output surface of the illuminated turbid medium object with a plurality of detection patterns. The controller is adapted to control the variable structured light detector for the variable structured light detector to use a detection pattern corresponding to an illumination pattern of the illuminated turbid medium object. The light detector is further adapted to optically measure a combination of retrieved light from the plurality of detection points as an optical measurement. The controller is further adapted to store an illumination pattern identifier indicative of the illumination pattern, a detection pattern identifier indicative of the detection pattern and the corresponding optical measurement.

21 Claims, 5 Drawing Sheets

(51) Int. Cl.
*A61B 5/00* (2006.01)
*G01N 21/17* (2006.01)

(56) References Cited

U.S. PATENT DOCUMENTS

| | | | |
|---|---|---|---|
| 6,958,815 B2 | 10/2005 | Bevilacqua et al. | |
| 2002/0049372 A1* | 4/2002 | Diab | 600/322 |
| 2005/0023356 A1* | 2/2005 | Wiklof et al. | 235/462.42 |
| 2006/0092414 A1* | 5/2006 | Geshwind et al. | 356/310 |
| 2006/0184043 A1 | 8/2006 | Tromberg et al. | |
| 2007/0083093 A1* | 4/2007 | Diab | 600/310 |
| 2008/0079802 A1 | 4/2008 | Nilson et al. | |
| 2008/0101657 A1* | 5/2008 | Durkin et al. | 382/110 |
| 2009/0118622 A1 | 5/2009 | Durkin et al. | |
| 2010/0292931 A1* | 11/2010 | Wang et al. | 702/19 |
| 2010/0310259 A1* | 12/2010 | Meyers et al. | 398/130 |
| 2011/0124988 A1* | 5/2011 | Cuccia | 600/310 |
| 2011/0263955 A1* | 10/2011 | Narita et al. | 600/341 |
| 2012/0065519 A1* | 3/2012 | Mincu et al. | 600/476 |

OTHER PUBLICATIONS

A. Yodh and B. Chance, "Spectroscopy and imaging with diffusing light," Physics Today, vol. 48, 1995, pp. 40, 34.

D.J. Cuccia, F. Bevilacqua, A.J. Durkin, and B.J. Tromberg, "Modulated imaging: quantitative analysis and tomography of turbid media in the spatial-frequency domain," Optics Letters, vol. 30, Jun. 2005, pp. 1354-1356.

J. Weber, D. Cuccia, and B. Tromberg, "Modulated Imaging in Layered Media," Engineering in Medicine and Biology Society, 2006. EMBS '06. 28th Annual International Conference of the IEEE, 2006, pp. 6674-6676.

PCT/CA2010/001445 international preliminary report.

PCT/CA2010/001445 international search report with claims 1-21.

S.D. Konecky, G.Y. Panasyuk, K. Lee, V. Markel, A.G. Yodh, and J.C. Schotland, "Imaging complex structures with diffuse light," Optics Express, vol. 16, Mar. 2008, pp. 5048-5060.

S.R. Arridge, "Optical tomography in medical imaging," Inverse Problems, vol. 15, 1999, pp. R41-R93.

V.A. Markel and J.C. Schotland, "Inverse problem in optical diffusion tomography. I. Fourier-Laplace inversion formulas," Journal of the Optical Society of America. A, Optics, Image Science, and Vision, vol. 18, Jun. 2001, pp. 1336-1347.

V.A. Markel and J.C. Schotland, "Inverse problem in optical diffusion tomography. II. Role of boundary conditions," Journal of the Optical Society of America A, vol. 19, Mar. 2002, pp. 558-566.

V.A. Markel, V. Mital, and J.C. Schotland, "Inverse problem in optical diffusion tomography. III. Inversion formulas and singular-value decomposition," Journal of the Optical Society of America A, vol. 20, May. 2003, pp. 890-902.

X. Intes, J. Ripoll, Y. Chen, S. Nioka, A.G. Yodh, and B. Chance, "In vivo continuous-wave optical breast imaging enhanced with Indocyanine Green," Medical Physics, vol. 30, Jun. 2003, pp. 1039-1047.

\* cited by examiner

METHOD AND SYSTEM FOR OPTICAL DATA ACQUISITION AND TOMOGRAPHY IMAGING OF A TURBID MEDIUM OBJECT

TECHNICAL FIELD

The invention relates to the field of optical imaging. More specifically, the invention relates to the field of optical imaging of a turbid medium object.

BACKGROUND

The advent of new biomedical imaging technique has enabled significant progresses in how we image humans and animals. In particular, the emergence in the mainstream of new modalities, such as diffuse optical tomography (DOT) has enabled researchers to image hemodynamic in vivo in a non invasive fashion. The relative low absorption and low scattering in the 600-1000 nm spectral range allow detection of photons travelling through several centimeters of biological tissue. Coupled with accurate models of light propagation, the NIR techniques enable imaging of deep tissue with boundary measurements using non-ionizing, low dose radiation. Applications of clinical significance have emerged for this modality, among those; breast cancer detection and neuronal activation measurement for cognitive studies are applications currently being actively pursued. By using different wavelengths, it is possible to map changes in hemodynamic and oxygenation levels to changes in light intensity. Diffuse optical tomography can also be performed with the combination of contrast agents absorbing light or having fluorescent properties. The imaging problem then aims to also recover the contrast agent localization and concentration.

Optical biomedical DOT imaging includes illuminating the tissue or turbid medium object with a light source and measuring the light leaving the tissue with a detector. Typically, such as described in U.S. Pat. No. 6,958,815 and US patent applications 2006/0184043 and 2009/0118622, a model of light propagation in the medium is developed and parameterized in terms of the unknown optical properties, scattering and/or absorption and/or concentration of the contrast agent, as a function of position in the tissue. The imaging problem consists in recovering the optical parameters, namely absorption, scattering, agent concentration, by using distinct illumination and detection positions.

The reconstructed image is a three-dimensional map of optical properties including endogenous absorption, scattering or fluorescence and exogenous compounds (absorption or fluorescence). With these reconstructed images, physiological measures can be performed such as blood oxygen saturation, blood volume, contrast agent concentration and dynamical uptake. These images enable to establish important physiological measurements such as metabolic activity, angiogenesis, hypoxia and pH, hyper-metabolism, micro-calcifications, protein expression.

Until now, optical mammography has mostly been implemented by positioning a series of local light sources and detection points at different positions on the breast surface depending on the configuration. In some implementation, a circular configuration of sources and detectors are used in combination with a multiplexing scheme. In others, sources and detectors are positioned in reflection or in opposite sides of parallel plates compressing the breast. In the latter configuration, the sources can be scanned mechanically or optically (with galvanometer mirrors) providing high-density measurements. The detection in this configuration can be done with either discrete detectors or a sensitive camera. These imaging techniques have a drawback however: to get dense measurements one has to scan or multiplex every light position, thereby limiting the frame rate.

SUMMARY

An improved diffuse optical tomography system and method for in vivo non-contact imaging is described herein. According to one aspect of the system, the system has an illumination source for illuminating a turbid medium object, a first spatial light modulator for projecting light patterns onto the turbid medium object and a second spatial light modulator to capture a spatially modulated response.

According to another aspect, the system has only one spatial light modulator to capture a spatially modulated response from a turbid medium object. The turbid medium object being illuminated by a light source. The light source can be an endogenous light source such as a bioluminescent light source. The light source can also be an exogenous light source such as an independent light source or an independent light source adapted to excite a fluorescent marker that is located within the turbid medium object.

According to another aspect, the system further has one or many light sensors to capture the response and a model of light propagation to optimize patterns to be projected and detected on the sample.

In the prior art, illumination modulation "pure tones" or spatial frequencies are used diminishing the rate at which measurements can be done (due to the pulse-width modulation of the micromirrors necessary to create light intensity levels) while detection is not modulated.

According to one aspect of the system, simple "on-off" mirror patterns are used, to obtain an increased switching speed (from 60 Hz to 10 kHz). By doing so, it becomes possible to get sufficient data for accurate image reconstruction at high frame rate. As an example, an approximation of the Fourier measures or spatial tones above can be used but any pattern can be generated at high speed. It is thus possible to illuminate and detect only the relevant modes necessary for image reconstruction.

Besides only illuminating and detecting the relevant modes, there are significant advantages to this new approach when compared to techniques of the prior art. First, by using wide-field illumination, it is possible to increase the light intensity while preserving the American National Standard Institute (ANSI) limit for tissue exposition since the limit is per area. Second, although higher total light intensity is used, it is spatially distributed and the maximum intensity of all points in the volume imaged is lower than the light intensity necessary in local illumination schemes to obtain equivalent signal to noise ratio. This has the advantage of decreasing bleaching effects for potential fluorescence applications while still increasing Signal to Noise Ratio (SNR).

According to one aspect of the system a Digital Micromirror Device (DMD) is used to modulate light for both illumination and detection. Thus it is possible to limit the measurements to only those necessary and recollimate the light detected to spread it in distinct spectral components providing spectral measurements without time penalty. The addition of time-domain or frequency domain measurements also becomes straightforward since only discrete detectors are necessary.

BRIEF DESCRIPTION OF THE DRAWINGS

The invention will be better understood by way of the following detailed description of embodiments of the invention with reference to the appended drawings, in which.

DETAILED DESCRIPTION

Figure 1:
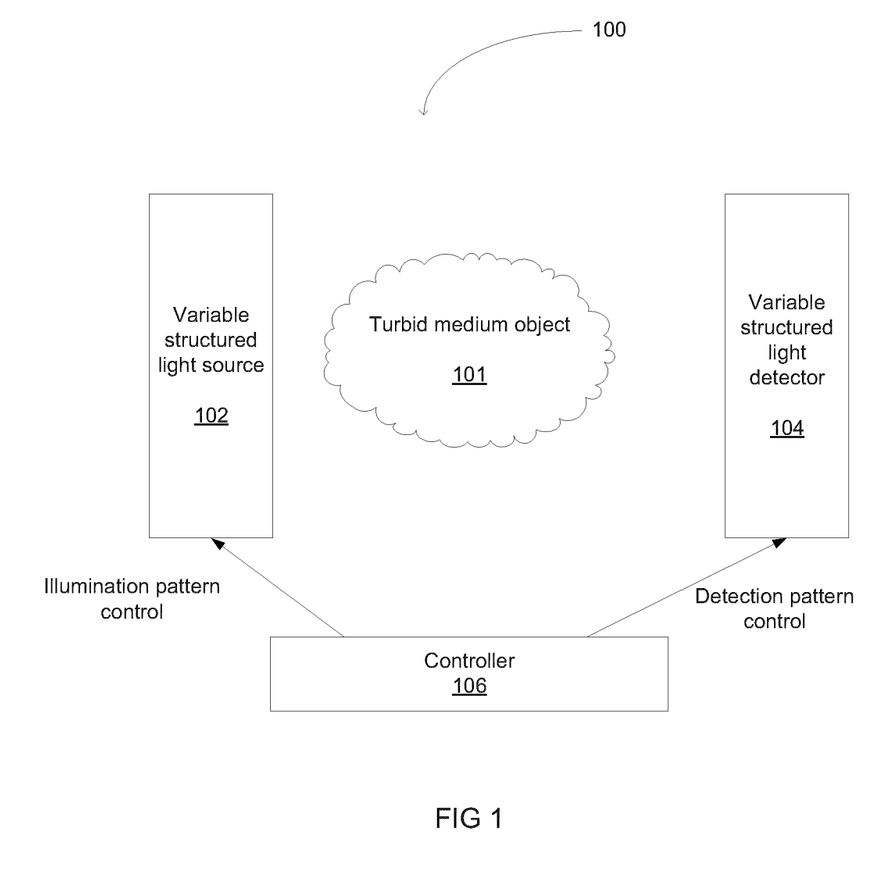
FIG. 1 is a block diagram of a system for optical data acquisition of a turbid medium object, according to an embodiment.

Presented in FIG. 1 is a system 100 for optical data acquisition of a turbid medium object 101. The turbid medium object 101 is represented here as an object having the shape of a cloud. However the object 101 can be any shape of object that has at least one turbid medium such as an animal tissue or human tissue. In one example, the system 100 is for acquiring data of a breast tissue. In another example, the system 100 is for acquiring data of a brain tissue. In another example, the system 100 is for acquiring data for whole body animal tissue.

According to FIG. 1, the system 100 has a variable structured light source 102 and a variable structured light detector 104 that are each placed on either side of the object 101. A skilled person will understand that rather than being placed on either side of the object 101, the light source 102 and the light detector 104 can be placed differently with respect to the object 101 such as on the same side. The light source 102 must however be placed so as to be able to project at least some light onto and through the object 101 and the light detector 104 must be placed so as to retrieve light from the object 101.

The light source 102 is adapted to project onto an input surface a plurality of illumination patterns and the light detector 104 is adapted to retrieve with a plurality of detection patterns a light from a plurality of detection points. The detection points are located on an output surface of the object 101. The light detector 104 is then adapted to optically measure a combination of retrieved light from the plurality of detection points as an optical measurement.

Further presented in FIG. 1, the light source 102 and the light detector 104 are both controlled by a controller 106. The controller 106 is adapted to control both the light source 102 and the light detector 104 so that the light source 102 and the light detector 104 use a corresponding illumination pattern and detection pattern.

According to one embodiment, the controller sends to the light source 102 an illumination pattern control and to the light detector 104 a corresponding illumination pattern control. The illumination pattern control and the detection pattern control being sent in a controlled and synchronized manner.

According to another embodiment, the controller sends to the light source 102 an illumination pattern control that allows the light source 102 to use a plurality of illumination patterns and sends to the light detector 104 an illumination pattern control that allows the light detector 104 to use a plurality of detection patterns. The light source 102 and the light detector 104 are adapted to use in a synchronized manner a pattern pair (i.e. illumination pattern and corresponding detection pattern) of the plurality of illumination patterns and of the plurality of detection patterns.

A skilled reader will understand that it is possible for the system 100 to have other ways of controlling the light source 102 and the light detector 104 for using a predetermined or randomly selected pattern pair.

According to one embodiment, the controller 106 uses a model of light propagation to optimize the selection of the pattern pair. This allows limiting the number of optical measurements to be processed by the system 100 by only measuring the essential optical measurements necessary to perform further analysis such as to perform three-dimensional tomography.

According to another embodiment, identifiers of the pattern pairs used by the light source 102 and the light detector 104 are stored by the controller, and corresponding optical measurements are also stored by the controller. For each illumination pattern used by the light source 102 and for each corresponding detection pattern used by the light detector 104, there is a pattern identifier that is stored by the controller in association with the corresponding optical measurement.

According to yet another embodiment, a single identifier to the pattern pair used by the light source 102 and the light detector 104 is stored by the controller. The single identifier is a predetermined identifier to a predetermined pattern pair. In association with the single identifier, there is stored the corresponding optical measurement.

It will be understood by a skilled reader, that it is possible for another module apart from the controller 106 to store the pairs of pattern identifiers or the single identifier to a pattern pair in association with the corresponding optical measurement.

According to another system 100, there is only the variable structured light detector 104 and the controller 106. The detector 104 being adapted to retrieve light from a plurality of detection points of an output surface of an illuminated turbid medium object 101 with a plurality of detection patterns. It is possible for the illuminated turbid medium object 101 to be illuminated by an exogenous light such as an independent light source or by an endogenous light such as with a bioluminescent object 101. The detector 104 is adapted to optically measure a combination of retrieved light from the plurality of detection points as an optical measurement. The controller being adapted to control the variable structured light detector for the variable structured light detector to use a detection pattern corresponding to an illumination pattern of the illuminated turbid medium object 101.

According to one embodiment, the system 100 has an illumination pattern detector. The illumination pattern detector is adapted to optically detect an illumination pattern of the illuminated turbid medium object 101 and send to the controller an illumination pattern identifier indicated of the illumination pattern. The controller is adapted to store an illumination pattern identifier indicative of the illumination pattern, a detection pattern identifier indicative of the detection pattern and the corresponding optical measurement.

Figure 5:
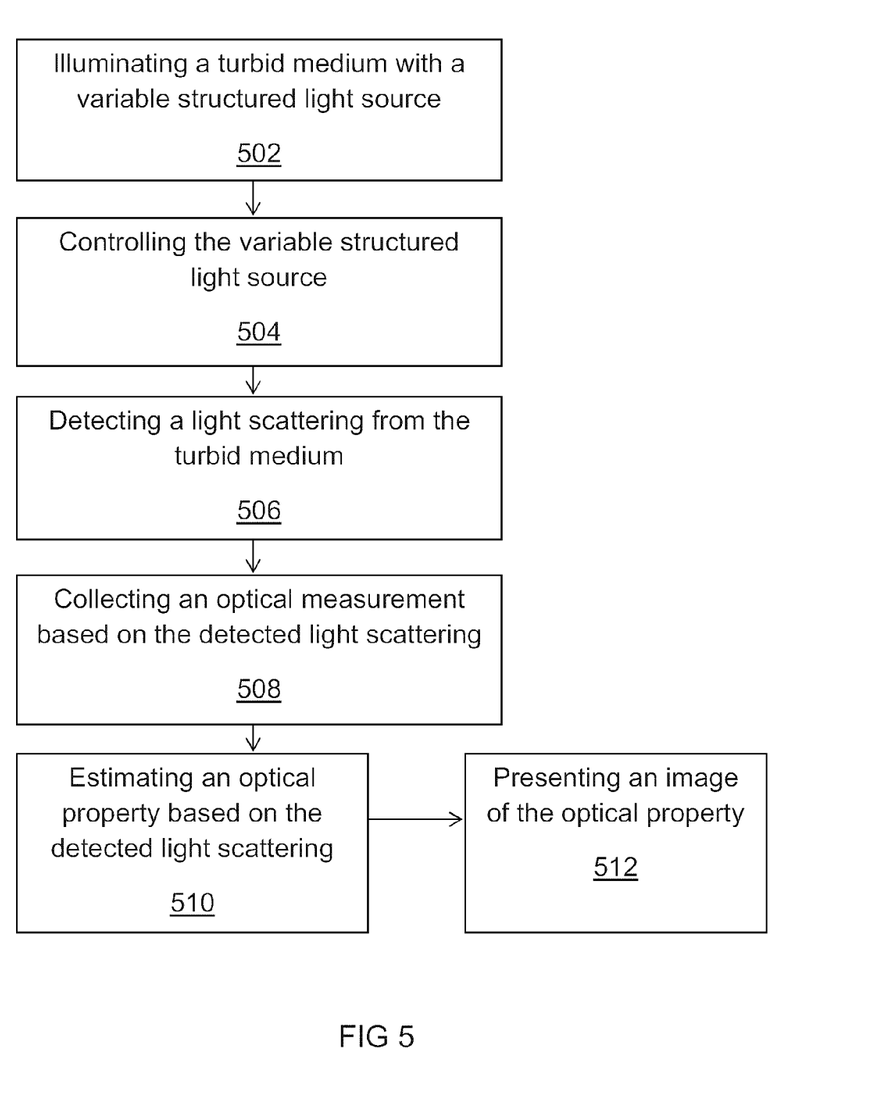
FIG. 5 is a flow chart of a method for optical data acquisition of a turbid medium object, according to an embodiment.

Presented in FIG. 5 is a method for optical data acquisition of a turbid medium object. The method comprises the steps of illuminating 502 a turbid medium with a variable structured light source, controlling 504 the variable structured light source, detecting 506 a light scattering from the turbid medium and collecting 508 an optical measurement based on the detected light scattering. The controlling 504 of the variable structure light source is done by modulating the variable structured light source based on a plurality of illumination patterns. The detecting 506 of a light scattering from the turbid medium is done with a detector that uses corresponding detection patterns to the illumination patterns. The collecting 508 of an optical measurement based on the detected light scattering is done according to the illumination patterns and the detection patterns.

According to another aspect, the method for optical data acquisition of a turbid medium object further comprises the step of estimating 510 an optical property based on the detected light scattering according to a reference model, a sensitivity matrix and the optical measurement.

According to yet another aspect, the method for optical data acquisition of a turbid medium object further comprises the step of presenting 512 an image of the optical property. The presentation of an imagine of the optical property can be done by various imaging systems such as a 3D imaging system, a fluorescence imaging system or a real-time imaging system.

Figure 2:
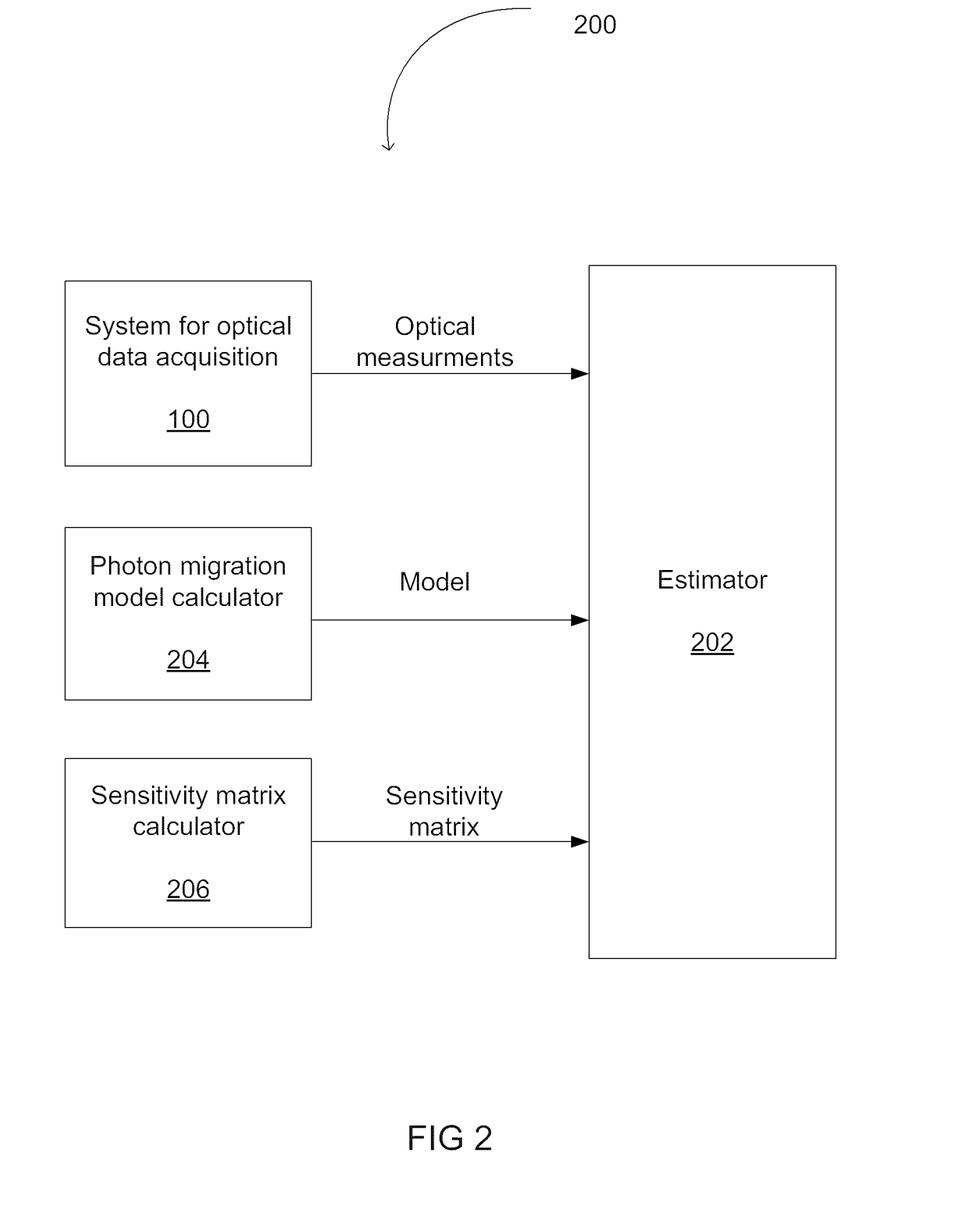
FIG. 2 is a block diagram of a system for tomography imaging of a turbid medium object, according to an embodiment.

Presented in FIG. 2, there is a tomography imaging system 200 of a turbid medium object 101. The tomography imaging system 200 has the system 100 for optical data acquisition of the turbid medium object 101, an estimator 202, a photon migration model calculator 204 and a sensitivity matrix calculator 206. The estimator 202 is adapted to determine an optical property based on the optical measurements taken by the system 100, on a model calculated by the model calculator 204 and on a sensitivity matrix calculated by the sensitivity matrix calculator 206.

The model calculator 204 provides a reference for the estimator based on the pattern pairs and optical measurements of a known medium. The model provided by the model calculator 204 has for each pattern pair a reference optical measurement that has been theoretically calculated for a known medium. The estimator 202 determines a difference between the reference optical measurement and the experimental optical measurement. According to one embodiment, the model is based on a theoretical measurement of a homogeneous absorbing and scattering medium. A skilled reader will however understand that it is possible for the system 200 to use another model that is based on either a theoretical or experimental measurement of any type of medium.

The sensitivity matrix calculator 206 uses a model of light propagation to relate the measurements for each pattern pairs to changes in one of the imaged parameter, absorption, diffusion or agent concentration. As a skilled reader will understand, it can be computed by either an approximation, such as the diffusion approximation, or based on accurate models such as Monte-Carlo simulations of light propagation or numerical solution of accurate models of light propagation, an example being the radiative transport equation. Based on the sensitivity matrix provided by the sensitivity matrix calculator, the estimator 202 is adapted to either amplify or reduce the established difference between the reference optical measurement and the experimental optical measurement. Moreover, based on the sensitivity matrix the estimator 202 is adapted to estimate an optical property of the turbid medium object in 3D.

Figure 4:
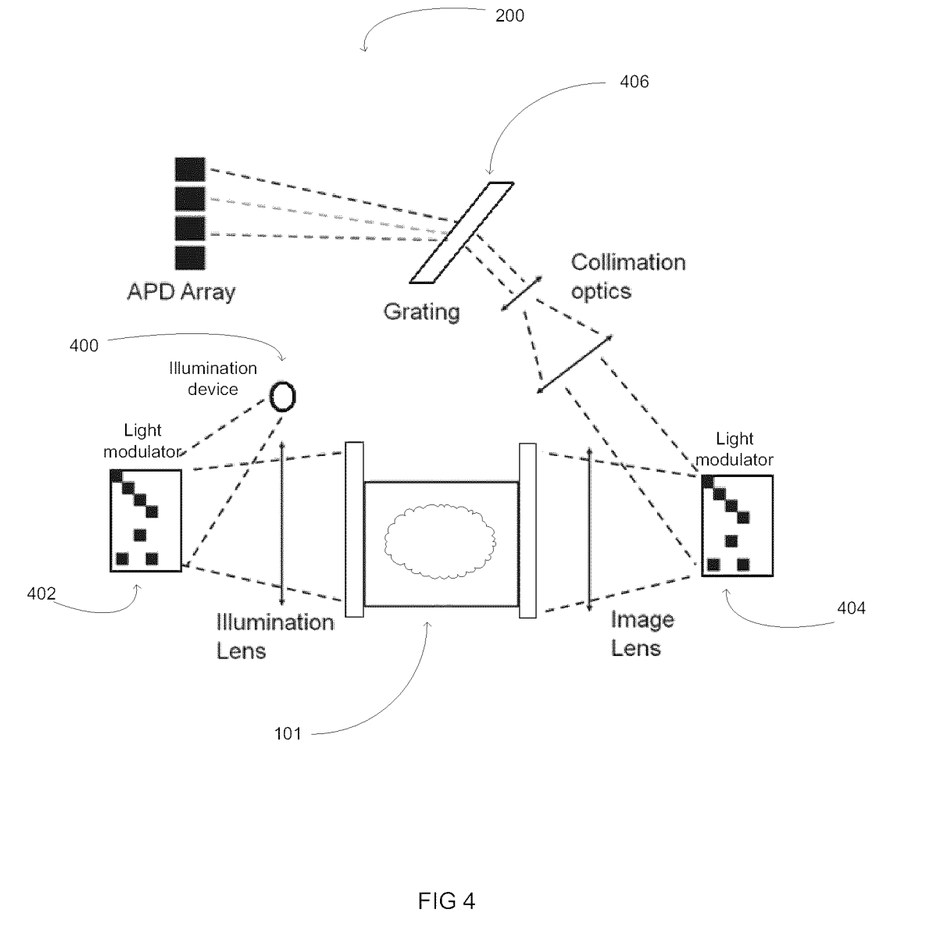
FIG. 4 is a block diagram of a system for tomography imaging of a turbid medium object having an illumination device and a first light modulator as a light source and a second light modulator as a light detector, according to an embodiment.

Presented in FIG. 4, according to one embodiment of the system 200, the light source 102 is an illumination device 400 that is coupled to a first light modulator 402 such as a digital micromirror for modulating light produced by the illumination device 400. The illumination device 400 can be a laser, a LED or a large spectral bandwidth source (i.e. white light or wide spectral source). This illumination is projected on the first light modulator 402 that is then imaged on the surface of the turbid medium object 101 to be imaged. At the same, or in a distinct location on the same turbid medium object 101, a second area is imaged onto a second light modulator 404 then focused and partially collimated into a single beam. This beam contains the sum of all detection points in the detection pattern determined by the second light modulator 404. This detection pattern is then detected directly by a single detector. Patterns of illumination and detection are then switched to a pre-determined sequence to form a measurement frame.

According to another embodiment, there is an illuminating micromirror board 102 and a detection micromirror board 104 that is used to integrate (sum) the light originating from a detection pattern. Both the illuminating micromirror board 102 and the detection micromirror board 104 have a two dimensional array of micromirrors. Sequential fast pattern switching on the array (e.g. 1024×768 mirrors, 1200×1900 mirrors or even more mirrors) are implemented in an onboard Field Programmable Gate Array (FPGA). A C++ interface 106 controls each micromirror board 102, 104 to generate the sequence of measurements at rates up to 10 kHz. A measurement is taken for each source-detector pair; all measurements are collated to form a frame. The frame rate is determined by the frame size. For example, for 64 source patterns and 64 detection patterns, a total of 64×64=4096 measurements are taken leading to a frame rate of 2.44 Hz. To perform image reconstruction, a sensitivity matrix can be pre-calculated for the set of patterns and its associated regularized pseudo-inverse is loaded in a large Graphical Computing Unit (GPU) to perform the matrix multiplication necessary for image recovery.

According to yet another embodiment of the system 100, 200, it is possible to acquire measurements for all source-detector pattern pairs of a frame in less than one second even where the number of source-detector pattern pairs is more than 1000 in number. Also it is possible for the estimator 202 to determine an optical property at a frame rate greater than 1 Hz.

According to one aspect, patterns will be dynamically changed from frame to frame to provide complementary information over time and diminish aliasing phenomena. The dynamical image, 3D+time, can be temporally filtered to generate higher accuracy spatial images.

It will be understood that the illumination source 102 can be continuous, frequency modulated or pulsed. Similarly, the detectors 104 used can detect continuous, modulated or can be time-correlated photon counters.

According to one embodiment, only a single detector 104 is used, this reduces significantly the cost of the optical tomography system 200. Also by using a fast detector 104 (e.g. a photomultiplier) it is possible to exceed frame rates obtainable by camera detection as used in previous art.

According to one embodiment, the illumination and detection are performed by geometry transmission at distinct sites on the turbid medium object 101 to be imaged. A potential use of this geometry is breast cancer imaging but other applications are also possible. Patterns can be optimized using a quantified criteria as described below for this configuration. An optical coupling medium, to control the dynamical range of the detection can be added but is not necessary.

According to another embodiment, the illumination and detection patterns are targeting the same area of the object 101 to be imaged and is referred to as reflection geometry. A potential use of this geometry is laminar optical tomography. Patterns can be optimized for this geometry according to a quantitative criteria. In this configuration, other optical filters, such as polarizers, can be added to the detection chain to reduce specular reflections.

A skilled person will understand that in all geometries, the application of the technique can be used with a single detector combined with a filter wheel to recover multiple wavelengths. This can be used to measure light absorption, diffusion or fluorescence intensity.

According to one embodiment, to measure distinct wavelengths and increase the frame-rate it is possible to spread the light emanating from the structured detection using an optical device 406, an example being a gratings, and use multiple detectors to measure in parallel a series of spectrally distinct components. Multiple discrete detectors can be used to image all wavelengths at the same time at no cost in frame rate.

According to another embodiment, the system 100 is optimized to measure a single or multiple fluorophores by exciting the sample with light and detecting the fluorescence emanating from the sample with a filter or other spectral separation device.

According to another embodiment, it is possible to remove the illumination to only measure light originating from the tissue 101. An application of this is bioluminescence imaging. This detection can be combined with one of the spectral separation technique described above.

In another embodiment, it is possible to use coherent light to generate spatial or temporal speckle patterns. These patterns can be detected by the structured detection to form images of blood flow. With this embodiment it is possible to measure the temporal or spatial auto-correlation of the electromagnetic field to recover a parameter related to blood flow. These blood flow measurements can be combined with the other mode of measurements to have a combined set of measurements.

It will be understood by a skilled reader that it is possible to use a mechanical device that moves the mirror around the object to be imaged to provide further measurements.

Figure 3:
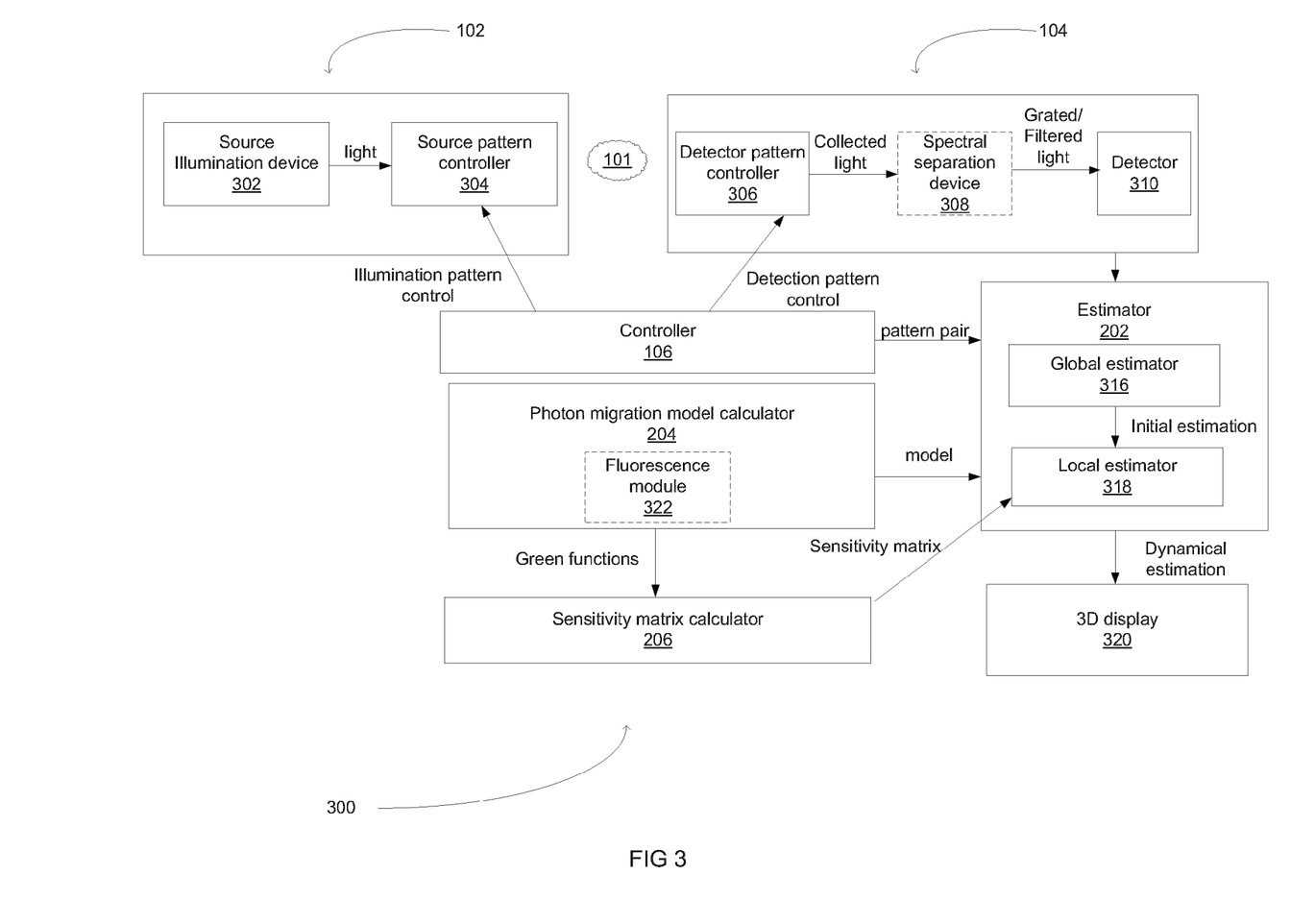
FIG. 3 is a block diagram of a system for tomography imaging of a turbid medium object having a 3D display, according to an embodiment.

In FIG. 3 there is presented a system 300 for tomography imaging, according to an embodiment. First a source illumination device 302 is used to illuminate a source pattern controller 304. In the current system 300, this controller 304 is a micromirror device but could be any other light modulation device. A separate controller 106 such as an acquisition controller is used to select which source pattern to apply. The choice of pattern to be applied is pre-determined using one of the pattern selection method described in the section below. The acquisition controller 106 is designed so that patterns can be changed at high temporal rates. It is responsible for the change of both illumination but also detection patterns simultaneously. The illumination and detection pattern controllers couple the source and detectors to the object 101 to be imaged. Upon modulation by the detector pattern controller 306, the collected light can be measured directly or preceded by a spectral separation device 308. Example spectral separation device 308 can be a filter wheel in combination with a single detector or a gratings combined with multiple detectors for simultaneous and rapid detection of many wavelengths.

A skilled reader will understand that it is possible for the detector to use a time domain detection process or a frequency domain detection process. Moreover, a skilled reader will understand that the detector can be adapted to detect a single wavelength for monospectral detection or to detect multiple wavelengths for multispectral detection.

A series of distinct source and detector pattern pairs can be measured and will be called a frame in the following. As an initial step, a photon-migration calculator 204 is used to provide an estimate of the theoretical measure for each pattern pair in the frame by assuming either a homogeneous absorbing and scattering medium or using a prior heterogeneous model based on prior information (e.g. MRI image). In all description below, this photon-migration calculator 204 can be based on numerical of analytical solutions of the diffusion equation, the radiative transport equation or Monte-Carlo simulations. The difference between the estimated measure by the calculator 204 and the experimental measure is then minimized to estimate by an estimator 202 various parameters such as: $\mu_a^0$ and $\mu_s^0$, or their spatial piecewise values in the case of heterogeneous prior information, i.e. the background optical properties by a global parameter estimator 316. This minimization is usually performed by a least-square estimator but other minimization techniques can be used. If more than one spectral channel is used, this procedure is repeated for each channel individually. All channels can also be combined with prior data about the object 101, an example being the absorption and scattering spectra of hemoglobin, to minimize physiological relevant parameters directly.

Once this initial estimation is performed, a second estimation is constructed based on the baseline optical parameters. Here the system 300 is used to image the object 101, with potentially varying optical contrast. The measurement frames are here taken in continuous mode to provide a successive series of frames. These can be acquired at high speed by synchronizing the pattern modulators and the detection. Since the set of frames is known prior to recording, by using the pattern selection techniques described below, an image reconstruction matrix can be pre-computed for each frame by using a well known perturbation technique such as the Born or Rytov approximation. To do so, the photon-migration calculator 204 is used to compute green functions for individual illumination and detection patterns. These Green functions are multiplied point by point in 3D to form a sensitivity matrix 206. This latter matrix can be normalized with the homogeneous green function to eliminate experimental factors. The matrix is then used to generate a so-called forward model by which measurements are generated for different configurations of absorption and scattering. This perturbative computations can be extended to more sophisticated models by using numerical techniques such as Monte Carlo or Finite Element Modeling.

The image reconstruction problem is solved by using a local estimator 318 of optical properties. This estimator 318 uses the forward matrix and adds regularization or prior information (e.g. Tikhonov regularization, truncated singular value decomposition) to generate an inverse multiplicative model. This inverse matrix is then used to multiply the measured data for each frame, at high speed to generate real-time images on a display 320. This can be done by using a multi-core CPU or another parallel computing device such as a GPU. This increased frame rate can then be used to monitor changes in optical parameters over time.

While the image reconstruction problem for real-time display uses a linear multiplication, better non-linear reconstruction schemes can be devised offline to recover optical properties more accurately and the same data can be analyzed in post-processing.

The acceleration of the image reconstruction process is due to the fact that by using a pair of optical modulators, for both detection and illumination, only relevant measures that are used in the image reconstruction problem are measured. By taking a lower number of measurements to recover equal image quality, the frame rate is increased significantly and cost are reduced due to the small number of detection channels that are necessary.

According to another embodiment, the system 300 is adapted to accommodate fluorescence imaging by using filters with strong attenuating power at the illumination wavelength. The photon-migration model calculator 204 is augmented with a fluorescence module 322 to account for interaction of light with the fluorophore. Initial optical parameters at both illumination and detection wavelengths can be estimated as above. Then by illuminating at the excitation wavelength of the fluorophore and detecting at the emission wavelength, a real-time 3D image of fluorophore changes can be generated by a similar process and a normalized Born fluorescence technique.

According to yet another embodiment, the system 300 is adapted to accommodate flow imaging by using a coherent light source. The source illumination device 302 is a coherent light source and the detection channel is used to measure temporal speckle patterns with an auto-correlator for example, or spatial speckle patterns, by varying the detection modulation. The photon migration model calculator 204 is also a coherence estimator, the global estimator 316 is a speckle estimator and the local estimator 318 is a local estimator of blood flow in a volume. The speckle patterns are combined with the photon-migration and coherence estimator to generate local 3D estimates of blood flow by constructing a reconstruction matrix as above.

In all these embodiments, by choosing the correct patterns for the variable structured light source 102 and the variable structured light detector 104, a lower number of measures are needed to reconstruct the image and the frame rate is increased.

Pattern Selection

Pattern selection can be performed by a multitude of methods. Each hardware geometry configuration, optimal images will be obtained by a specific choice of illumination and detection patterns.

A first method to find optimal patterns is to model the choice on an analytical approximation of the problem as found in (eq 7). The block diagonal form (eq 7) can be exploited to directly measure the relevant Fourier modes for image reconstruction. Once the modes that will be used are selected, pre-computed regularized inverse matrices can be used to provide real-time images. The regularization technique can be truncated pseudo-inverse, Tikhonov, Bayesian or any known regularization in the field. This technique can be readily modified to include a realistic model of light propagation, for example Monte-Carlo simulations, or the radiative transport equation. Since generating Fourier modes takes more time with current modulators, an alternative can use binary patterns to accelerate the pattern changes on the sample.

A second method is to use a singular value decomposition of the linear problem using all measures, or a subset thereof, to generate measurement Eigen-vectors that optimally constrain the reconstruction problem. These Eigen-vectors can be directly projected on the sample to provide an optimal set of measurements. The procedure to generate the tomographic images is the same as above with a pre-computed inverse used to accelerate the reconstructions.

A third method can choose to optimize measurements so that they produce an incoherent forward model matrix as is used in the technique of compressed sensing. The tomographic image can be recovered in a basis of functions that is sparse with respect to the recovered images and measurements are chosen to provide incoherent projections in this basis. Image reconstruction is then performed by a minimization algorithm based on the notion of sparsity of the solution.

A fourth method of optimization is to use experiments, numerical or real, with a large set of patterns and a known phantom to compare the different choices with a reconstruction metric.

Environment

The data to be measured can be selected to optimise the problem of image reconstruction. As such, the ability to relay only the relevant information or measures to a display device, which can be a computer or a specific display device, in real-time and performing the image reconstruction in real-time. The addition of a real-time display of the 3D images can be included for a single channel or all channels when using a multispectral system.

The system 100, 200, 300 allows rapid imaging of a full 3D image. The system 100, 200, 300 is further adapted to use the temporal data to extract pharmaco-kinetic parameters related to an injected compound. The latter can be a fluorescent compound or absorber.

In applications to pre-clinical imaging, this system 100, 200, 300 can be combined with an anaesthesia module and a stereotaxic device. According to one embodiment, the system 100, 200, 300 is combined with a gas chamber to provide gas to an animal as it is being imaged.

The system 100, 200, 300 can also be combined with a stimulation device to elicit responses in synchrony with a chosen stimulations.

Image Formation

In the diffusion approximation to the radiative transport equation, the propagation of light in tissues (valid if $\mu_a \ll \mu_s'$) is modeled by a diffusion equation for the fluence $\phi$ $$[-\nabla \cdot D(r)\nabla + c\mu_a(r)]\phi(r) = S(r) \quad (1)$$

where $D(r) = D_0 = 1/(3\mu_s')$ is the diffusion coefficient that will be assumed constant in the following, $\mu_a(r)$ the absorption coefficient, c the speed of light in the medium and S(r) a source located on the boundary. To completely define the problem, boundary conditions are specified by $$\phi + l n \cdot \nabla \phi = 0 \quad (2)$$

where n is an outward normal to the boundary and/is an extrapolation distance. In the slab geometry, the source and detectors lies in the planes, $r_s = (\rho_s, z_s = 0)$ and $r_d = \rho_d, z_d = d)$ with $\rho_{s,d}$ are two dimensional vectors in the surface on which measures are made. Define the Green function $$[-\nabla \cdot D_0 \nabla + c\mu_a(\vec{r})]G(\vec{r}, \vec{r}') = \delta(\vec{r} - \vec{r}'). \quad (3)$$

Then if using the Rytov approximation and denoting $\mu_a(r) = \mu_a^0 + \delta\mu_a(r)$, the following equation relates the measures to variations in absorption $$\phi(\vec{r}_s, \vec{r}_d) = -G_0(\vec{r}_s, \vec{r}_d)\ln\left(\frac{I(\vec{r}_s, \vec{r}_d)}{I_0(\vec{r}_s, \vec{r}_d)}\right) = \int G_0(\vec{r}_d, \vec{r})G_0(\vec{r}_s, \vec{r})c\delta\mu_a(\vec{r})d^3\vec{r} \quad (4)$$

where I and $I_0$ are respectively the measured intensities of the perturbed and unperturbed sample (with time-varying changes, the baseline would be defined at the beginning of the temporal changes). A very similar technique is to use the Born approximation to linearize the reconstruction problem. Discretizing the integral in (eq. 4), the approximate linear forward model relating measured to changes in absorption $\delta\mu_a(r)$ can be inverted by a regularized pseudo-inverse or other techniques.

The identification of the best measures is not straightforward. When working with extended structured source and detectors, a first estimate of optimal patterns can be obtained by using approximation (eq. 4) and assuming translational symmetry in the x-y directions. Define the Fourier transform in the spatial coordinates that are "in-plane", i.e. $\rho_{s,d}$, as $$G(\rho, \rho', z, z') = \int \frac{d^2q}{(2\pi)^2} g(q; z, z') e^{iq\cdot(\rho'-\rho)} \quad (5)$$

Equation (4) can be written:

$$\tilde{\phi}(\vec{q}_d, \vec{q}_s) = c \int_0^d g(\vec{q}_s; z_s, z) g(\vec{q}_d; z, z_d) \delta\mu_a(\vec{q}_s + \vec{q}_d, z) dz \quad (6)$$

Taking into account the boundary conditions, simple rewriting leads to, $$F_n(q) = \tilde{\phi}(\vec{q}/2 + \vec{p}_n, \vec{q}/2 - \vec{p}_n) = \quad (7)$$
$$\int_0^d dz g(\vec{q}/2 + \vec{p}_n, z, 0) g(\vec{q}/2 - \vec{p}_n, z, 0) \delta\mu_a(q; z)$$

Where $q = q_s + q_d$ and $p_n = (q_s - q_d)/2$. The Fourier transform provides a block-diagonalized form and can be numerically estimated for each q. This formulation is used to image a complex phantom by scanning a source with a galvo-mirror and taking large set of measurements with a sensitive camera. While a dense set of measures is used ($3 \times 10^8$), much fewer combinations of these measures are actually used in the reconstruction formula (eq. 7) since both q and $p_n$ are discretized. Thus, according to one aspect of the current invention, it is possible to generate directly the functions $F_n(q)$ for a series of q's, only the data used in the inversion formula are measured.

It should be noted however that the method above is limited in two aspects: First the Rytov or Born techniques approximate absorption changes. This limitation is usually lifted by using non-linear numerical models, for example finite elements methods or boundary elements methods to recover optical parameters by a non-linear algorithm.

The second aspect is the diffusion approximation (e.g. for small spatial volumes where the diffusion approximation does not hold). By using other techniques such as Monte-Carlo simulations or the radiative transport equation, it is possible to handle these cases.

What is claimed is:

1. A system for optical data acquisition of a turbid medium object, the system comprising:
    a variable structured light source, the light source being adapted to illuminate an input surface of the turbid medium object with a plurality of illumination patterns;
    a variable structured light detector, the light detector being adapted to retrieve light from a plurality of detection points of an output surface of the turbid medium object with a plurality of detection patterns, the light detector being further adapted to optically measure a combination of retrieved light from the plurality of detection points as an optical measurement; and
    a controller adapted to control the variable structured light source and the variable structured light detector for the variable structured light source and the variable structured light detector to use an illumination pattern corresponding to a detection pattern, the controller being further adapted to store an illumination pattern identifier indicative of the illumination pattern, a detection pattern identifier indicative of the detection pattern and the corresponding optical measurement.

2. The system as claimed in claim 1 wherein the optical measurement for all pairs of the illumination patterns and the detection patterns is acquired in less than one second, the pairs being more than 1000 in number.

3. The system as claimed in claim 2, wherein the structured light source and the structured light detector comprise a micromirror device having a two-dimensional array of micromirrors.

4. A system for tomography imaging of a turbid medium object, the system comprising:
    a variable structured light source, the light source being adapted to illuminate an input surface of the turbid medium object with a plurality of illumination patterns;
    a variable structured light detector, the light detector being adapted to retrieve light from a plurality of detection points of an output surface of the turbid medium object with a plurality of detection patterns, the light detector being further adapted to optically measure a combination of retrieved light from the plurality of detection points as an optical measurement;
    a controller adapted to control the variable structured light source and the variable structured light detector for the variable structured light source and the variable structured light detector to use an illumination pattern corresponding to a detection pattern, the illumination pattern and the corresponding detection pattern being a pattern pair, the controller being further adapted to store an illumination pattern identifier indicative of the illumination pattern, a detection pattern identifier indicative of the detection pattern and the corresponding optical measurement; and
    an estimator adapted to determine an optical property based on a reference model, a sensitivity matrix and the optical measurement.

5. The system as claimed in claim 4 wherein the optical measurement for all pattern pairs is acquired in less than one second, the pattern pairs being more than 1000 in number, the estimator being adapted to determine the optical property at a frame rate greater than 1 Hz.

6. The system as claimed in claim 5, wherein the structured light source and the structured light detector comprise a micromirror device having a two-dimensional array of micromirrors.

7. The system as claimed in claim 4, wherein the estimator comprises a store of precalculated matrices corresponding to each one of the pattern pairs.

8. A method for optical data acquisition, the method comprising:
    illuminating a turbid medium with a variable structured light source;
    controlling the variable structured light source by modulating the variable structured light source based on a plurality of illumination patterns;
    detecting a light scattering from the turbid medium with a detector that uses corresponding detection patterns to the illumination patterns; and
    collecting an optical measurement based on the detected light scattering according to the illumination patterns and the detection patterns.

9. A method for tomography imaging, the method comprising:
    illuminating a turbid medium with a variable structured light source;
    controlling the variable structured light source by modulating the variable structured light source based on a plurality of illumination patterns;
    detecting a light scattering from the turbid medium with a detector that uses corresponding detection patterns to the illumination patterns;
    collecting an optical measurement based on the detected light scattering according to the illumination patterns and the detection patterns; and estimating an optical property based on the detected light scattering according to a reference model, a sensitivity matrix and the optical measurement.

10. The method as claimed in claim 9 further comprising presenting an image of the optical property with a 3D imaging system.

11. The method as claimed in claim 9 further comprising presenting an image of the optical property in real-time.

12. The method as claimed in claim 9 further comprising presenting an image of the optical property with a fluorescence imaging system.

13. The method as claimed in claim 9 wherein the detecting comprises combining the detected light scattering into a single beam, the beam having a sum of all detection points in the detection pattern.

14. The method as claimed in claim 9 wherein the detecting comprises time domain detection.

15. The method as claimed in claim 14 wherein the detecting uses a single wavelength detector for monospectral detection.

16. The method as claimed in claim 14 wherein the detecting uses a multi wavelength detector for multispectral detection.

17. The method as claimed in claim 9 wherein the detecting comprises frequency domain detection.

18. A system for optical data acquisition of an illuminated turbid medium object, the system comprising:

a variable structured light detector, the light detector being adapted to retrieve light from a plurality of detection points of an output surface of the illuminated turbid medium object with a plurality of detection patterns, the light detector being further adapted to optically measure a combination of retrieved light from the plurality of detection points as an optical measurement; and a controller adapted to control the variable structured light detector for the variable structured light detector to use a detection pattern corresponding to an illumination pattern of the illuminated turbid medium object, the controller being further adapted to store an illumination pattern identifier indicative of the illumination pattern, a detection pattern identifier indicative of the detection pattern and the corresponding optical measurement.

19. The system as claimed in claim 18 further comprising an illumination pattern detector adapted to send to the controller an illumination pattern identifier indicative of the illumination pattern.

20. The system as claimed in claim 18 wherein the illuminated turbid medium object is a bioluminescent object.

21. The system as claimed in claim 18 wherein the structured light detector comprises a micromirror device having a two-dimensional array of micromirrors.

* * * * *